United States Patent [19]

Allen, Jr. et al.

[11] 4,293,554

[45] Oct. 6, 1981

[54] METHOD OF TREATING ASTHMA

[75] Inventors: George R. Allen, Jr., Old Tappan, N.J.; John W. Hanifin, Jr.; Daniel B. Moran, both of Suffern, N.Y.; Jay D. Albright, Nanuet, N.Y.

[73] Assignee: American Cyanamid Company, Stamford, Conn.

[21] Appl. No.: 122,958

[22] Filed: Feb. 21, 1980

[51] Int. Cl.$^3$ .............................................. A61K 31/495
[52] U.S. Cl. ................................................... 424/250
[58] Field of Search ........................................ 424/250

[56] References Cited

U.S. PATENT DOCUMENTS 3,915,968 10/1975 Bellasio et al. ................. 424/250 X

OTHER PUBLICATIONS

Chemical Abstracts, 83:193361p (1975).

Primary Examiner—Leonard Schenkman
Attorney, Agent, or Firm—Edward A. Conroy, Jr.

[57] ABSTRACT

A method of treating asthma in a warm-blooded animal using the compound 6-phenyl-1,2,4-triazolo[4,3-b]pyridazin-3(2H)-one.

1 Claim, No Drawings

METHOD OF TREATING ASTHMA

DESCRIPTION OF THE INVENTION

This invention is concerned with a method of treating asthma in warm-blooded animals which comprises the administration of the compound 6-phenyl-1,2,4-triazolo[4,3-b]pyridazin-3(2H)-one, whose structure is given below.

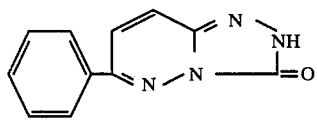

This compound is disclosed as an intermediate in Derwent Abstract J7-5017-076 where the utility of the final products is as depressants.

It has now been discovered that this compound is effective in treating asthma in warm-blooded animals as determined by the following test which measures antiasthma activity by the mouse passive cutaneous anaphylaxis (PCA) test.

PREPARATION OF IMMUNOGLOBULIN G (IgG)

Female Swiss Webster mice (Buckberg) were immunized by intraperitoneal injection of 10 mg. of ovalbumin (Miles Lab. Code 95051, Batch 21) in 0.5 ml. of 50% saline-50% Freunds complete adjuvant (Difco Lab.). The mice were boosted with the same antigen preparation one and two weeks later. Forty days after the original immunization the mice were sacrificed by decapitation and serum collected. The serum was pooled, heated at 56° C. for 4 hours and titered to obtain a 2 hour PCA lesion slightly greater than one cm. in diameter. The challenge was 0.1 mg. DNP-ovalbumin.

PREPARATION OF IMMUNOGLOBULIN E (IgE)

Female B6×D2 F1 mice (Jackson Labs.) were given an intraperitoneal injection of 0.5 ml. of saline with one µg. of dinitrophenylated ovalbumin and one mg. of aluminum hydroxide gel (Wyeth Amphogel). Preparation of the DNP-ovalbumin (approx. 2 DNP/molecule) is described in the next paragraph. One and two months later the mice were boosted with the same antigen preparation. One week after the second boost, the mice were sacrificed by decapitation and serum collected. The serum was pooled and titered to obtain a 48 hour PCA lesion slightly greater than one cm. in diameter.

PREPARATION OF DNP-OVALBUMIN

One gram of ovalbumin, 1.0 g. of potassium carbonate and 1.0 g. of dinitrobenzene sulfonic acid were dissolved in 50 ml. of water. The solution was shaken for 18 hours at 37° C. and then placed in a cellophane dialysis bag and dialyzed versus three changes of 0.9% saline at 4° C. The protein concentration was determined by the method of Lowry, et al., J. Biol. Chem., 193, 265 (1951). The content of DNP groups was determined from the absorbance at 365 nm (extinction coefficient=18500). The DNP-ovalbumin prepared by this method contained $4.4 \times 10^{-5}$ moles of DNP/gram of protein or 1.9 residues per ovalbumin molecule.

PASSIVE CUTANEOUS ANAPHYLAXIS TEST

At −50 hour (relative to antigen challenge at 0 hour) 50 µl. of IgE is injected intradermally on the left side of a 25 g. female mouse, posterior to the axilla at the level of the diaphragm. At −2 hour, 50 µl. of IgG is injected intradermally on the right side of the mouse. The mice are then placed in individual cages and randomly assigned to control or treatment groups. Challenge and reading are performed in serial order so that reading of the assay is essentially blind. At −1 hour, the control animals received an intraperitoneal injection of 0.5 ml. of a 0.05% solution of carboxymethylcellulose in saline. For treatment animals, the test compound is dissolved or suspended in the carboxymethylcellulose-saline solution and administered intraperitoneally at −1 hour at 2, 10 or 50 mg./kg. At 0 hour, the mice are anesthetized with ether and 0.5 ml. of saline containing 0.1 mg. of DNP-ovalbumin antigen and 2.5 mg. of Evans blue dye is injected into the tail vein. At +15 minutes the mice are sacrificed by cervical dislocation, the dorsal skin is removed and the blue PCA spots are examined on the inside surface. The largest and smallest diameters of the lesion and a qualitative estimate of intensity of color are recorded. The mean of the products of diameters (area) for mice in a given treatment group are compared with the control group. IgE and IgG lesions are analyzed independently. If the area for a treatment group is significantly smaller than the lesion area for the control group for either IgE or IgG lesion, the test compound is considered to be active as an anti-asthma agent.

The compound 6-phenyl-1,2,4-triazolo[4,3-b]pyridazin-3(2H)-one is active by the criterion of this test.

Another test which determines anti-asthma activity is by measuring the inhibition of histamine release from human blood basophils as described below.

REAGENTS

8% Perchloric acid—A 100 ml. portion of 60% perchloric acid is added to 650 ml. of water.

Human Albumin—Sigma Chemical Co.

Calcium and Magnesium Stocks—Made to 0.075 M and 0.5 M respectively using calcium chloride dihydrate and magnesium chloride hexahydrate.

10× Concentrated Tris Buffer—Contains 140.3 g. of sodium chloride, 7.45 g. of potassium chloride and 74.5 g. of Trizma-Tris Pre-Set, Reagent Grade, pH 7.6, at 25° C. (Sigma Chemical Co.) per 2000 ml. distilled water.

Tris-A Buffer—A 10 ml. portion of 10× concentrated tris buffer and 1.0 ml. of human serum albumin diluted to 100 ml. with water.

Tris-ACM Buffer—A 10 ml. portion of 10× concentrated tris buffer, 1.0 ml. of human serum albumin, 0.8 ml. of calcium stock and 0.2 ml. of magnesium stock, diluted to 100 ml. with water.

Rabbit Antihuman IgE—Behring Diagnostics. Prepared at a 10 µg. protein/ml. concentration.

Ragweed Antigen E—NIH Research Reference Branch. Prepared at a 0.01 µg. protein/ml. concentration.

House Dust Mite Extract (Dermatophagoides Farinae)—Hollister-Stier Lab. The 1:100 (w:v) allergenic extract is diluted 1:1,000 or 1:10,000 before use.

Other Allergens—Intradermal solutions or intramuscular preparations for hyposensitization. Hollister-Stier Lab. Final concentration is one PNU/ml.

SEPARATION OF LEUKOCYTES FROM HUMAN BLOOD AND CHALLENGE

An 80 ml. portion of blood is drawn from humans with known histamine release to anti-IgE, ragweed antigen or other specific allergen, using four 20 ml. heparinized Vacutainer tubes (Becton Dickinson Inc.). The 80 ml. of blood is mixed with 20 ml. of saline containing 0.6 g. of dextrose and 1.2 g. of dextran. The blood is allowed to sediment in two 50 ml. polycarbonate centrifuge tubes until a sharp interface develops between the red cells and plasma (60–90 minutes). The plasma is withdrawn from each tube and transferred to 50 ml. polycarbonate tubes. This plasma is centrifuged at 4° C. and 110× gravity for eight minutes and then the supernatant is removed as completely as possible. The cell button is resuspended in 2 to 3 ml. of Tris-A buffer using a siliconized Pasteur pipet with a bulb attached and drawing the liquid gently in and out of the pipet with the tip below the liquid until an even suspension of cells is obtained. The suspension is then diluted to 50 ml. with Tris-A buffer and centrifuged as described above. Repeat this procedure one more time. The supernatant is removed and the cell button resuspended in 2 to 3 ml. of Tris-ACM buffer and transferred to a polycarbonate flask with additional Tris-ACM buffer. The cells are placed in a 37° C. water bath and uniform suspension is maintained by frequent swirling. The reaction tubes, containing anti-IgE or antigen alone, or anti-IgE or antigen plus test compound in 0.2 ml. total volume are also placed in a 37° C. water bath. One ml. of a uniform suspension of the cells is added to each tube and the tubes are incubated for 60 minutes at 37° C., vortexing the tubes gently every 15 minutes to maintain suspension. The reaction tubes are then centrifuged at 4° C. and 1500 r.p.m. for 10 minutes. One ml. of the supernatant is decanted into 3 ml. polyethylene tubes and 0.2 ml. of 8% perchloric acid is added to each tube. Blank tubes and total tubes are included in each test. Blank tubes have all the reagents including cells except that which releases histamine (i.e., antigen or anti-IgE). The total tubes are made up by adding 1.0 ml. of cells in triplicate to 0.2 ml. of 8% perchloric acid. The volume is adjusted to equal that of reaction tubes by adding an appropriate amount of Tris-ACM buffer.

ASSAY OF RELEASED HISTAMINE BY THE AUTOMATED FLUOROMETRIC METHOD

This procedure is based on the method of Siraganian, R. P., J. of Immunological Methods, 7, 283 (1975) and is based on the manual method of Shore, P. A., et al., J. of Pharmacology, 127, 182 (1959).

The automated system consists of the following Technicon Autoanalyzer II components: Sampler IV; Dual Speed Proportioning Pump III; Fluoronephelometer with a narrow pass primary filter 7-60 and a secondary filter 3-74; Recorder and Digital Printer. The manifold described by Siraganian (vide supra) is employed with the following modifications: the dialyzer is omitted; all pumping tubes pass through a single proportioning pump with large capacity and twice the volume of sample is taken for analysis. The automated chemistry consists of the following steps: extraction from alkaline saline into butanol; back extraction into dilute hydrochloric acid by addition of heptane; reaction of histamine with o-phthaldialdehyde at high pH and conversion of the o-phthaldialdehyde adduct to a stable fluorophore with phosphoric acid. The reaction product is then passed through the fluorometer. The full scale response is adjusted to 50 mg. histamine base with a threshold sensitivity of approximately 0.5 mg.

ASSAY OF RELEASED HISTAMINE BY ISOTOPE ENZYME ASSAY

This assay method has been described in detail by Snyder, et al., J. of Pharm. and Exp. Therapeutics, 153, 544 (1966).

A crude preparation of histamine N-methyl transferase is made from guinea pig brain. The supernatant for histamine assay is mixed with 0.2 $\mu$Ci 3-H-histamine (New England Nuclear Inc.), 0.05 $\mu$Ci 14C-S-adenosylmethionine (New England Nuclear Inc.) and 50 $\mu$l. of methyl transferase. The mixture is incubated for one hour at 37° C. and the reaction is stopped by the addition of 2 ml. of 1 N sodium hydroxide. The solution is then saturated with sodium chloride and the methyl histamine formed is extracted into 6 ml. of chloroform. The organic phase is separated and washed with 2 ml. of 1 N sodium hydroxide. The organic phase is poured into a scintillation vial and allowed to evaporate to dryness. A one ml. portion of ethanol is added to dissolve the residue and 10 ml. of Aquasol counting fluid (New England Nuclear Inc.) is added. The vials are counted in a Nuclear Chicago Mark I liquid scintillation counter for both tritium and carbon-14 and the ratio (dpm $^{14}$C/dpm $^{3}$H) is computed. A standard curve of the ratio for several concentrations of histamine (1–200 ng.) is prepared and the amount of histamine in the cell supernatants is read from this curve.

CALCULATION OF THE RESULTS OF HISTAMINE RELEASE

For fluorometric assays the instrument blank is subtracted from the ng. histamine of each sample.

For isotope assays the $^{14}$C/$^{3}$H ratio is computed for each sample and the ng. histamine read from a standard curve. Then the ng. histamine of each sample is divided by the mean of the three totals (cells lysed with perchloric acid) to obtain percent release.

Control samples contain antigen but no compound. Blank (or spontaneous release) samples contain neither antigen nor compound. The mean of the blanks (three replicates) is subtracted from the percent release for controls and compounds.

The mean for control and compound groups is computed and the result for a test compound computed as % of control of the formula:

$$100 \times \frac{\% \text{ histamine release with compound}}{\% \text{ histamine release with controls}}$$

A compound is considered active if the IC$_{50}$ (the concentration of compound which inhibits the histamine release by 50%) is 0.1 mM or less.

The compound 6-phenyl-1,2,4-triazolo[4,3-b]pyridazin-3(2H)-one is active by the criterion of this test.

GUINEA PIG LUNG FUNCTION TEST

Female Hartley-strain guinea pigs, averaging 250 g. are injected with 2 ml. of an emulsion comprising 50 mg. of ovalbumin, one ml. of saline and one ml. of complete Fruend's adjuvant. Twenty-eight days later the animals are sacrificed and their blood collected in 50 ml. tubes. After clotting and clot retraction, the tubes are centrifuged at 2100 r.p.m. for 20 minutes. The sera are then pooled and stored in one ml. aliquots at −70° C.

The antibody levels of these pooled sera are estimated by determining the dilution of the antibody that gives a 100 mm$^2$ lesion in a guinea pig passive cutaneous anaphylaxis; typically a dilution of 1:4000 to 1:8000 is found to give this size lesion.

At −24 hours (relative to antigen challenge at 0 time), 2 ml. of saline containing 0.05 ml. of IgG hyperimmune serum are injected intraperitoneally into 250–300 g. female Hartly-strain guinea pigs. One hour before challenge the test compound is given to 10 animals as an intraperitoneal injection of 4 ml./kg. of a suspension in 0.5% carboxymethylcellulose. The standard dose is 50 mg./kg. Ten other animals receive the vehicle as control. The challenge consists of an intravenous bolus of 2 mg. ovalbumin in one ml. of saline. The time of injection, time to first observable symptom of anaphylaxis and time to loss of righting reflex are recorded for each animal. Thirty minutes after the challenge the numbers of dead and living animals are also recorded.

The treated and control groups are compared by a Mann-Whitney rank sum test for the time to symptom and time to collapse. In addition, a Fischer's exact test is done on the number of survivors vs. dead for control and treated groups. If any of these comparisons are significant, the test compound is considered active.

The compound 6-phenyl-1,2,4-triazolo[4,3-b]pyridazin-3(2H)-one is active by the criterion of this test.

The novel compound of the present invention has thus been found to be highly useful for meliorating asthma when administered in amounts ranging from about 1.0 mg. to about 100.0 mg. per kilogram of body weight per day. A preferred dosage regimen for optimum results would be from about 5.0 mg. to about 50.0 mg. per kilogram of body weight per day, and such dosage units are employed that a total of from about 0.35 g. to about 3.5 g. of active compound for a subject of about 70 kg. of body weight are administered in a 24 hour period. The dosage regimen may be adjusted to provide the optimum therapeutic response. For example, several divided doses may be administered daily or the dose may be proportionally reduced as indicated by the exigencies of the therapeutic situation. This active compound may be administered by intravenous, intramuscular, or subcutaneous routes, and also by inhalation therapy including aerosol sprays.

Compositions according to the present invention having the desired clarity, stability and adaptability for parenteral use are obtained by dissolving from 0.10% to 10.0% by weight of the active compound in a vehicle consisting of a polyhydric aliphatic alcohol or mixtures thereof. Especially satisfactory are glycerin, propylene glycol, and polyethylene glycols. The polyethylene glycols consist of a mixture of non-volatile, normally liquid, polyethylene glycols which are soluble in both water and organic liquids and which have molecular weights of from about 200 to 1500. Although the amount of the active compound dissolved in the above vehicle may vary from 0.10 to 10.0% by weight, it is preferred that the amount of the active compound employed be from about 3.0 to about 9.0% by weight. Although various mixtures of the aforementioned non-volatile polyethylene glycols may be employed, it is preferred to use a mixture having an average molecular weight of from about 200 to about 400.

In addition to the active compound, the parenteral solutions may also contain various preservatives which may be used to prevent bacterial and fungal contamination. The preservatives which may be used for these purposes are, for example, myristyl-gamma-picolinium chloride, benzalkonium chloride, phenethyl alcohol, p-chlorophenyl-α-glycerol ether, methyl and propyl parabens, and thimerosal. As a practical matter, it is also convenient to employ antioxidants. Suitable antioxidants include, for example, sodium bisulfite, sodium metabisulfite, and sodium formaldehyde sulfoxylate. Generally, from about 0.05 to about 0.2% concentrations of antioxidant are employed.

For intramuscular injection, the preferred concentration of the active compound is 0.25 to 0.50 mg./ml. of the finished compositions. The novel compound of the present invention is equally adapted to intravenous administration when diluted with water or diluents employed in intravenous therapy such as isotonic glucose in appropriate quantities. For intravenous use, initial concentrations down to about 0.05 to 0.25 mg./ml. of active ingredient are satisfactory.

EXAMPLE 1

6-Phenyl-1,2,4-triazolo[4,3-b]pyridazin-3(2H)-one

A mixture of 196.11 g. of 3-benzoylpropionic acid, 60 ml. of hydrazine hydrate and one liter of ethanol is stirred at reflux for 18 hours, then cooled in an ice bath, giving 167 g. of 6-phenyl-4,5-dihydro-3(2H)-pyridazinone as a cream colored solid.

The 167 g. of the above pyridazinone is partially dissolved in 600 ml. of acetic acid. A solution of 50 ml. of bromine in 100 ml. of acetic acid is added portionwise while warming on a steam bath over a period of one hour. The mixture is heated for an additional hour, then poured into crushed ice. The resulting solid is filtered, washed with water and air dried, giving 148 g. of 6-phenyl-3(2H)-pyridazinone as a cream colored solid.

A mixture of 147.5 g. of 6-phenyl-3(2H)-pyridazinone and 800 ml. of phosphorus oxychloride is heated on a steam bath for 5 hours and then concentrated free of excess phosphorus oxychloride. The concentrate is diluted with cold water and the resulting solid is filtered, washed with water and air dried, giving 158 g. of 3-chloro-6-phenylpyridazine as a pinkish solid.

A mixture comprising 10.0 g. of the above pyridazine, 11.4 g. of ethyl carbazate and 200 ml. of butanol is stirred at reflux for 5 days, then cooled in an ice bath. The resulting solid is filtered and air dried then dissolved in ethanol and filtered. The filtrate is treated with charcoal, filtered and this filtrate cooled in an ice bath giving 2.35 g. of the desired product as yellow crystals, m.p. 255°–257° C.

We claim:

1. A method of preventing the development of asthmatic conditions in a warm-blooded animal, which comprises administering to said animal a prophylactically effective amount of 6-phenyl-1,2,4-triazolo-[4,3-b]pyridazin-3(2H)-one.

* * * * *